US007222961B2

(12) United States Patent
Soliz et al.

(10) Patent No.: US 7,222,961 B2
(45) Date of Patent: May 29, 2007

(54) METHOD FOR DETECTING A FUNCTIONAL SIGNAL IN RETINAL IMAGES

(75) Inventors: Peter Soliz, Albuquerque, NM (US); Eduardo S. Barriga, Albuquerque, NM (US)

(73) Assignee: Kestrel Corporation, Albuquerque, NM (US)

( * ) Notice: Subject to any disclaimer, the term of this patent is extended or adjusted under 35 U.S.C. 154(b) by 710 days.

(21) Appl. No.: 10/628,292

(22) Filed: Jul. 28, 2003

(65) Prior Publication Data
US 2004/0114109 A1 Jun. 17, 2004

Related U.S. Application Data

(60) Provisional application No. 60/401,224, filed on Aug. 5, 2002.

(51) Int. Cl.
*A61B 3/00* (2006.01)
*A61B 3/10* (2006.01)
*A61B 3/14* (2006.01)
*A61B 5/00* (2006.01)
*A61B 13/00* (2006.01)

(52) U.S. Cl. .................. 351/200; 351/205; 351/206; 351/213; 351/221; 600/318; 600/320; 600/558

(58) Field of Classification Search ................ 351/200, 351/205, 206, 213, 221, 246; 600/318, 320, 600/558
See application file for complete search history.

(56) References Cited

U.S. PATENT DOCUMENTS

| 4,922,919 A | 5/1990 | Novack |
| 5,219,400 A | 6/1993 | Jacot et al. |
| 5,297,554 A | 3/1994 | Glynn et al. |
| 5,308,919 A | 5/1994 | Minnich |
| 5,912,723 A * | 6/1999 | Maddess ..................... 351/246 |

(Continued)

FOREIGN PATENT DOCUMENTS

WO    WO 2004/012576 A3 *   2/2004

OTHER PUBLICATIONS

International Preliminary Examination Report (PCT/IPEA/409) prepared for PCT/US03/2390 on Dec. 6, 2004.*

(Continued)

*Primary Examiner*—David N. Spector
(74) *Attorney, Agent, or Firm*—Janeen Vilven; Peacock Myers, P.C.

(57) ABSTRACT

A system and method for detecting a functional signal in retinal images. An optical imaging device comprises a stimulation light source, an interrogating light source, and a detector. The retina is stimulated by the stimulation light source. The retina is then illuminated by an interrogation light, and the reflected intensity from the retina is measured at an interrogating spectral band that indicates the state of hemoglobin saturation before and after visual stimulation. The optical changes that result from retinal neuronal activity are captured by the detector. The signal representing the state of hemoglobin saturation before and after visual stimulation is isolated. In an embodiment of the present invention, this signal is isolated using principle components analysis (PCA). In another embodiment of the present invention, blind source separation (BSS) and independent component analysis (ICA) algorithms such as extended spatial decorrelation and fast-ICA are used to isolate the functional signal from the retinal videos.

20 Claims, 15 Drawing Sheets

U.S. PATENT DOCUMENTS

| | | | |
|---|---|---|---|
| 6,086,206 | A | 7/2000 | Sutter |
| 6,276,798 | B1 | 8/2001 | Gil et al. |
| 6,315,414 | B1 * | 11/2001 | Maddess et al. ............ 351/246 |
| 6,430,431 | B1 * | 8/2002 | De Yoe ....................... 600/410 |
| 6,478,424 | B1 | 11/2002 | Grinvald et al. |
| 6,556,853 | B1 | 4/2003 | Cabib et al. |

OTHER PUBLICATIONS

Deco, G., et al., "Non-linear feature extraction by redundancy reduction in an unsupervised stochastic neural network.", *Neural Networks*, vol 10, Issue 4,(Jun. 1997),683-691.

Heynen, H., "Origin of the oscillatory potentials in the primate retina", *Vision Res.*, vol. 25, Issue 10,(1985),1365-73.

Stetter, M., et al., "Blind signal separation from optical imaging recordings with extended spatial decorrelation.", *IEEE Transactions on Biomedical Engineering*, vol. 47, No. 5,(May 2000),573-577.

Stetter, M., et al., "Principal component analysis and blind separation of sources for optical imaging of intrinsic signals.", *NeuroImage*, vol. 11, Issue 5,(May 2000),482-490.

Scheb1,M. et al., Blind Signal Separation from Optical Imaging Recording with Extended Spatial Decorrelation, IEEE Transactions on Biomedical Engineering, vol. 47, No. 5, May 2000.

G. Decco and L. Parra, Non-Linear Feature by Redundancy Reduction in an Unsupervised Stochastic Neural Network, Neural Networks, vol. 4., pp. 683-691, 1997. Great Britain.

Henny Heynen et al., Origin of the Oscillatory Potentials in the Primate Retina, Vision Res. vol. 25, No. 10, pp. 1365-1373, 1985, Great Britain.

* cited by examiner

METHOD FOR DETECTING A FUNCTIONAL SIGNAL IN RETINAL IMAGES

CROSS REFERENCE TO OTHER APPLICATIONS

This application claims benefit under 35 U.S.C. § 119(e) of provisional application No. 60/401,224, filed Aug. 5, 2002, which is incorporated by reference herein, in its entirety, for all purposes.

FIELD OF INVENTION

The present invention relates generally to a process for detecting functional signal in retinal images. More particularly, the present invention relates to a process for extracting the functional signal from the background noise via advanced statistical techniques yielding a functional signal from retinal activation in the presence of noise from other sources.

BACKGROUND OF THE INVENTION

Visual field testing (perimetry) is the most widely used method for detecting and monitoring progression of diseases of the optic nerve (i.e. glaucoma, ischemic optic neuropathy, compressive optic neuropathy) and retina. Perimetry is a functional test of the subject's vision. The shape and extent of the defect on the visual field map allows the clinician to confirm the presence of damage, helps to localize where the damage is along the visual pathway (retina, optic nerve, chiasm, optic tract, postgeniculate fibers), and is essential in monitoring progression or improvement over time.

However, perimetry remains a subjective test that requires the subject to make important judgments during the test that can be clouded by anxiety, fatigue, or lack of concentration. A second problem with the current perimetry tests is that almost 40-50% of the optic nerve may be damaged before a significant perceptual change can be detected on the visual field test, making it relatively insensitive for detecting early damage when intervention may still save vision. A third problem is that the visual field test is highly variable in areas of defects where damage has occurred, making it difficult to monitor changes.

New methods are needed to improve the sensitivity for detection of damage and change over time. Objective methods would also provide more reliable determination of the status of the visual system. A number of new technologies have emerged in recent years in an attempt to fill this need and have included multifocal electroretinography (MERG), pattern electroretinography (PERG), visual evoked potential (VEP), multifocal visual evoked potentials (MVEP), and pupil perimetry.

Traditionally, neuronal activity in the central nervous system including the retina has been recorded electrically. Recently however, noninvasive optical recording of neuronal signals from the brain has been demonstrated. Intrinsic changes in the optical properties of active brain tissue (referred to as "intrinsic signals") permit visualization of neuronal activity when the surface of brain tissue is directly imaged using sensitive CCD cameras. Intrinsic signals refer to the change in the percent reflectance of illuminating (or interrogating) light occurring as a result of the change in the absorption coefficient due to the conversion of oxyhemoglobin to deoxyhemoglobin in response to the metabolic demands of active neurons. The interrogating light is band-restricted to wavelength(s) where the difference in absorption spectra between the oxyhemoglobin and deoxyhemoglobin molecule is the greatest, for example, typically in the region of 580-700 nm. Other sources of the intrinsic signals include changes in the microcirculation and light scattering that are also dependent on neuronal activity.

The intrinsic signals from the brain are usually very small (0.1 to 1.0% of the overall reflected light intensity). However, when appropriately imaged, they can have high spatial resolution (50 microns) corresponding to the areas of active neuronal activity. The small intrinsic signals are isolated from the noise using image subtraction techniques. By subtracting baseline (neuronally less active) images of the brain tissue from stimulated (neuronally active) images, small intrinsic functional signals can be isolated. With the use of optical techniques, it has been possible to record neuronal activities of the primate cortex in vivo.

Visual cortical neurons that are driven preferentially by one eye are grouped into a strip of cortex referred to as an ocular dominance column for that eye. The next strip of cortical cells is driven preferentially by the other eye and forms an adjoining ocular dominance column. These strips of ocular dominance columns alternate between the right and left eye and form a prominent part of the functional architecture of the primate visual cortex. The optical recording of intrinsic signals has allowed the ocular dominance columns to be directly visualized across the cortex in vivo. This was achieved by imaging the cortex with interrogating light, while providing visual stimuli to one eye and then the other. Ocular dominance column images are then constructed by subtracting right eye-stimulated images from the left eye-stimulated images. Optical recording of the temporal lobe of human patients undergoing neurosurgery has also been reported.

Optical recording of the retinal function is noninvasive and ideal for clinical application. The retina is a direct extension of the brain and part of the central nervous system. Neuronal activity of the retina is fundamentally similar to that of the brain. Like the brain, appropriate metabolic changes (changes in hemoglobin oxygen saturation and state of tissue cytochrome for example) can be detected in the retina in response to changes in corresponding reduction of oxyhemoglobin levels. However, the measured changes in reflectance in response to the visual stimulus are on the order of 0.1% to 1.0% of the total reflected intensity level that makes the functional signal difficult to detect by standard methods since it is masked by the other signals (noise) that are present.

What is needed is a practical, non-invasive system and method for revealing retinal function to aid in early detection of retinal and optic nerve diseases such as glaucoma and to monitor for progression of damage. Such a system and method would provide objective, quantitative, and localizing information in the form of a functional image of neuronal-activity across the retina thereby complementing and/or augmenting conventional perimetry. Finally, such a system and method would be instrumental in evaluating animal models of retinal and optic nerve disease and the response to treatment, where perimetry is impractical.

SUMMARY OF THE INVENTION

An embodiment of the present invention is a system and method for optical mapping of retinal function using retinal imaging. In this embodiment, the retina is stimulated in a selected spectral band (for example and without limitation 530 nm±5 nm) centered on the green maximum sensitivity of the retina under photopic conditions. The reflected intensity from the retina is measured at an interrogating spectral band that indicates the state of hemoglobin saturation before and after visual stimulation. To maximize the signal to noise ratio (SNR), an interrogation wavelength centered on, for example and without limitation, 700±20 nm was used, where retinal stimulation is minimal and the difference in absorption between oxyhemoglobin and reduced hemoglobin is greatest. The optical changes that result from retinal neuronal activity are mapped by registration of recorded CCD frames that have been corrected for noise effects (as more fully set forth below), with subsequent comparison of post-stimulation images from pre-stimulation images. In an alternative embodiment of the present invention, a hemifield of the retina is stimulated in the selected spectral band (530 nm±5 nm) centered on the green maximum sensitivity of the retina stimulated so that both stimulated regions of the retina and non-stimulated regions of the retina can be imaged simultaneously, thereby further reducing variability due to temporal recording of images. Variable stimulation patters may be used in either the hemifield stimulation or the full retinal stimulation to maximize the resultant reflectance recorded.

Data is analyzed using Principal Component Analysis (PCA), Independent Component Analysis (ICA) and Blind Source Separation (BSS) to estimate sources of variability from information in recorded images, even if those source are not completely statistically independent.

It is therefore an aspect of the present invention to measure retinal function using retinal imaging.

It is another aspect of the present invention to provide a standardized process to analyze functional retinal signals.

It is yet another aspect of the present invention to increase the sensitivity of current visual field testing methods.

It is yet another aspect of the present invention to improve diagnosis of eye disease with improved retinal images.

It is a further aspect of the present invention to isolate the signal representing the state of hemoglobin saturation before and after visual stimulation using principal component analysis (PCA).

It is yet another objective of the present invention to use Blind Source Separation (BSS) and Independent Component Analysis (ICA) to find the underlying factors associated with the recorded image data.

It is another aspect of the present invention to isolate the signal representing the state of hemoglobin saturation before and after visual stimulation using blind source separation algorithms.

It is yet another aspect of the present invention to apply non-linear independent component analysis to the separation of the sources present during the stimulation of the retina.

These and aspects of the present invention will become apparent from a review of the general and detailed description to follow.

An embodiment of the present invention is a system and method for optical mapping of retinal function using retinal imaging. In this embodiment, an optical imaging device of retinal function (OID-RF) comprises a stimulation light source, an interrogating light source, and a detector. Although a CCD sensor is illustrated in FIG. 1 herein, this is not meant as a limitation. Other detectors and recording media can also be used without departing from the methodology as illustrated herein. The retina is stimulated by a stimulation image produced by the stimulation light source. In an exemplary embodiment of the present invention, the stimulation image is projected in a spectral band (for example and without limitation 530 nm±5 nm) centered on the green maximum sensitivity of the retina under photopic conditions. The retina is then illuminated by an interrogation light and the reflected intensity from the retina is measured at an interrogating spectral band that indicates the state of hemoglobin saturation before and after visual stimulation. To maximize the signal to noise ratio (SNR), an interrogation wavelength centered on 700±20 nm was used, where retinal stimulation is minimal.

The optical changes that result from retinal neuronal activity are captured by the detector. The changes are mapped by registration of recorded image frames. The raw data is preprocessed to eliminate unwanted artifacts, such as blinking or excessive eye movement. Because the resulting signal from the retinal activation contains noise from other sources (for example, the non-stimulated retinal background and other unknown physiological changes), the data is further processed to remove noise. In an embodiment of the present invention, principal components analysis (PCA) is used to isolate the signal representing the state of hemoglobin saturation before and after visual stimulation. In another embodiment of the present invention, blind source separation (BSS) (using the extended spatial-decorrelation (ESD) algorithm) and independent component analysis (ICA) (using the Fast-ICA algorithm) are used to extract the functional signal from the retinal videos. By comparison of post-stimulation images from pre-stimulation images, and applying the data analysis techniques of the present invention, measurements of changes in blood perfusion due to neural activity resulting from visual stimulation of the photoreceptors in the human retina can be made, and hence the health status of the retina can be assessed.

DETAILED DESCRIPTION OF THE INVENTION

Independent component analysis (ICA) is a statistical and computational technique used to reveal hidden factors that underlie a set of random variables, in this case, measurements of reflectance from a retina. The goal is to recover independent sources given only the sensor observations that are unknown linear mixtures of the unobserved independent source signals. Thus ICA is use to analyze mulitvariate data stemming from the production of images of the retina. ICA is related to Principle Component Analysis (PCA) and factor analysis but is more capable of finding underlying sources or factors in a data set because it takes into account higher order statistical properties of the data. For example, PCA is a correlation based transformation of data. In contrast, ICA not only decorrelates the signals (i.e. $2^{nd}$ order statistics) but also reduces the higher order statistical dependencies (i.e. $4^{th}$ order cumulants) and attempts to make the signals detected as statistically independent as possible. In ICA, data sources are assumed to be linear mixtures of unknown variables.

Blind Source Separation (BSS) is a similar technique as ICA, but in this case only second order statistics are used. BSS and ICA are applied in the present invention to separate sources of variability present in images of the retina produced by the apparatus of the present invention.

Figure 1:
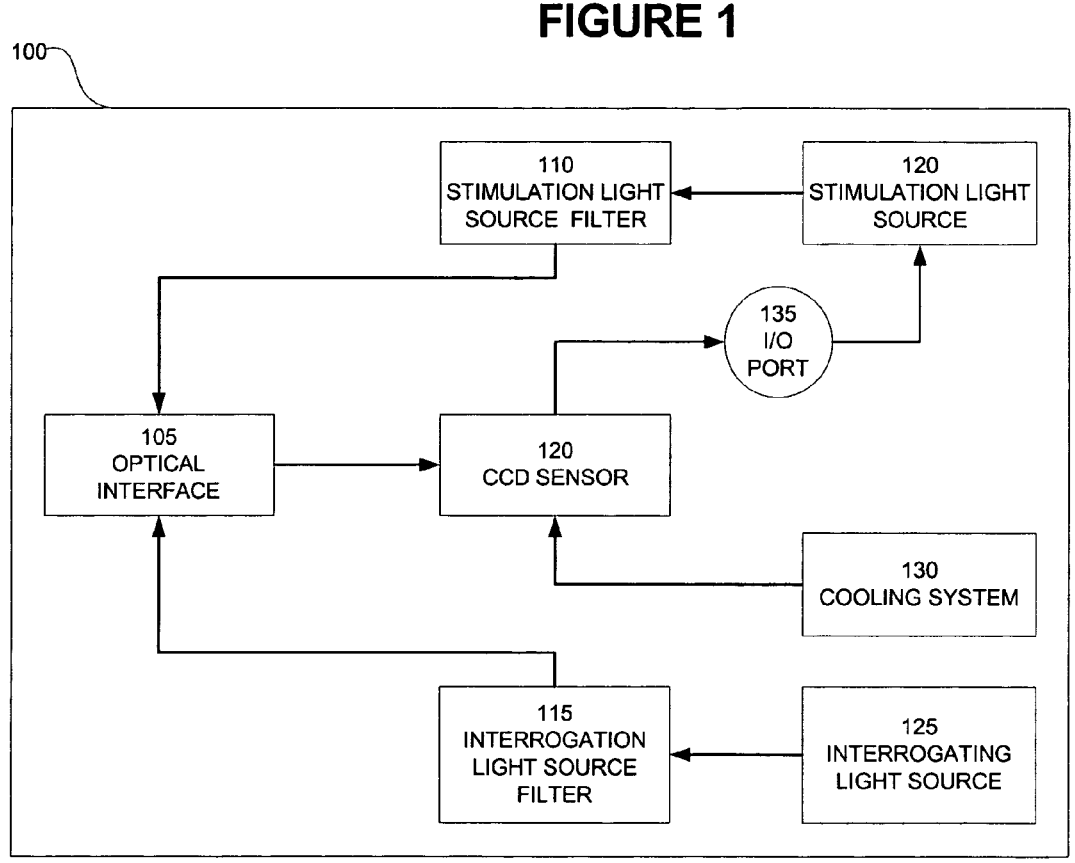
FIG. 1 illustrates a functional diagram of an optical imaging device of retinal function (OID-RF) according to an embodiment of the present invention.

An embodiment of the present invention is a system and method for optical mapping of retinal function using retinal imaging. FIG. 1 illustrates a functional diagram of an optical imaging device of a retinal function (OID-RF) 100 according to an embodiment of the present invention. An optical interface 105 receives the output of a stimulation light source filter 110 and the output of an interrogation light source filter 115. A stimulation light source 120 provides the input to the stimulation light source filter 110. An interrogation light source 125 provides the input to the interrogation light source filter 115. A detector 120 (herein illustrated as a CCD array) captures images received at the optical interface. The data captured by the detector 120 are sent to input/output (I/O) port. 135 where they may be captured by a memory device (such as a general purpose computer). The detector 120 is cooled by a cooling system 130 (if necessary, since certain detectors might not require cooling). The I/O port 135 also permits control of the stimulation light source 120 making it possible to use variable stimulation patterns (see FIG. 3).

Figure 2:
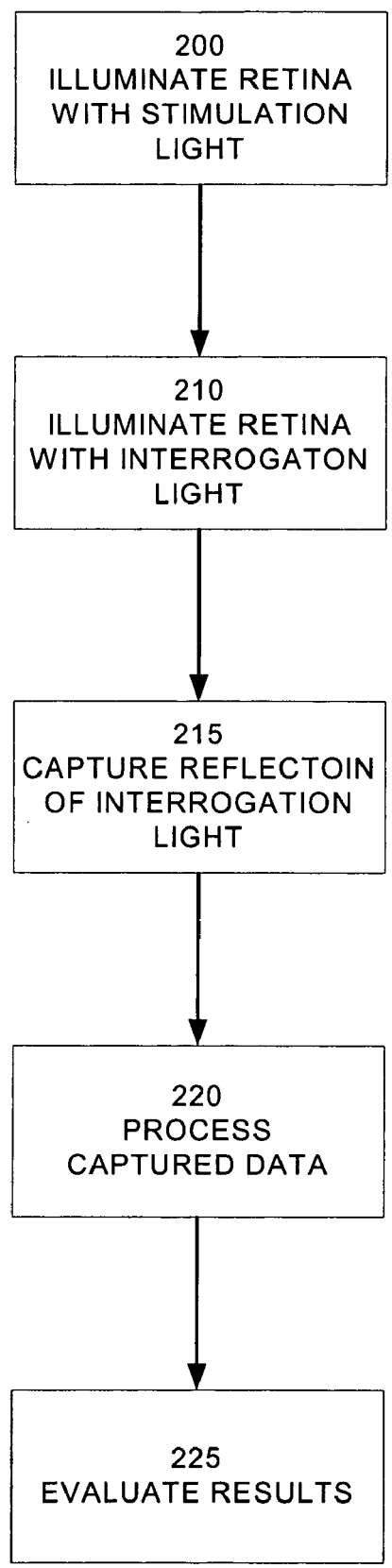
FIG. 2 illustrates the process by which a retina is mapped using an OID-RF according to an embodiment of the present invention.

Referring to FIG. 2, the process by which a retina is mapped using an OID-RF according to an embodiment of the present invention is illustrated. The retina is illuminated by a stimulation image produced by the stimulation light source 200. In an exemplary embodiment of the present invention, the stimulation image is projected in a spectral band (for example and without limitation 530 nm ±5 nm) centered on the green maximum sensitivity of the retina under photopic conditions. The method is not limited to use with any one OID-RF as any optical imaging device capable of projecting multiple patterns onto the retina at multiple wavelengths is suitable.

The retina is then illuminated by an interrogation light 210 and the reflected intensity from the retina is captured 215 at an interrogating spectral band that indicates the state of hemoglobin saturation before and after visual stimulation. In an exemplary embodiment of the present invention, an interrogation wavelength centered on 700±20 nm was used, where retinal stimulation is minimal and the signal to noise ratio (SNR) is maximized.

As noted above stimulation illumination can be over the entire retina or over a the superior or inferior retinal hemifield. The hemifield retinal stimulation permits internal controls within the eye to be established since only one half of the retina is subject to stimulation thus insuring that the reflectance measurements corresponding to the stimulated areas of retina and those of the simultaneously recorded non-stimulated retinal areas do not show the same change in optical signal. Further, the hemifield implementation of the present invention further eliminates a source of variability due to time difference between when a first non-stimulated image is taken and a second stimulated image (or vice versa). The implementation of the visual stimulus was via a standard PC-type computer driving a VGA video card with programming in a custom interactive computer language based on C. The stimulus computer communicated with the system controller computer via an RS-232 serial port. The VGA video card drove a LCD-type video projector that had been mounted on the Canon fundus camera.

Using the method of the present invention, the retina is stimulated and simultaneously measured during a variable second interval (5 seconds used in the example below) after a pre-stimulus baseline of retinal images is recorded. The stimulus period is preferably followed by an additional variable recovery period of recording. This data collection protocol is repeated a number of times for each eye with rest periods between each collection protocol. Various anomalies in imaging such as eye blinks. movements, dark frames are not used in the averaging of frames following each stimulus protocol. The two bands (stimulation at 530 nm and collection at 700 nm) are preferably separated using internal filters so that interference of the bands does not occur.

The number of images generated using the protocol described herein is not meant as a limitation. In fact, as higher collection frequencies are possible due to improvements in equipment this will further assist in quantifying the sources of noise in the system and lead to more accurate data. Thus it will be appreciated by those skilled in the art that higher frame counts used in averaging the imaging results are within the scope of the present invention.

The optical changes that result from retinal neuronal activity are captured by the detector image. The changes are mapped by registration of recorded detector image frames. The raw data is preprocessed 220 to eliminate unwanted artifacts, such as blinking or excessive eye movement and noise (for example, the non-stimulated retinal background and other unknown physiological changes). The results are evaluated 225 by comparing post-stimulation images with pre-stimulation images and measuring changes in blood perfusion due to neural activity resulting from visual stimulation of the photoreceptors in the retina.

Local firing activity of retinal neurons in response to a light stimulus can be mapped across the two dimensional plane of the retina by imaging the resulting changes in local oxygen consumption. Oxygen consumed by stimulated retinal cells causes a transient shift in the ratio of oxyhemoglobin to deoxyhemoglobin in the immediate microcirculatory region, which may consist of an initial depletion followed by a compensating increase. Local changes in the oxyhemoglobin level can be imaged by detecting small changes in the absorption (and hence, reflection) in an active spectral band at baseline (pre-stimulus) and comparing this to the reflection during and after stimulus. Retinal areas having reduced function would be expected to show less change in the spectral reflection of light at the same interrogation bands following a light stimulus as compared to surrounding areas of retina with normal function.

The optical measurements of local oxygen changes induced by neuronal activation are caused by changes in oxyhemoglobin levels within blood vessels supplying the retina. A dense sheet of capillaries derived from the central retinal artery circulation provides the main source of oxygen to the inner retina, where the retinal ganglion cells and axons are located. It is these cells that produce electrical spiking activity or action potentials. A second circulation to the retina, derived from the choroidal circulation, supplies photoreceptors in the outer retina. Unlike the inner retinal circulation, the choroidal circulation is a high-flow vascular bed with little change in oxyhemoglobin levels between the arterial and venous side.

The optical measurements obtained by the present invention depend on the characteristic spectral properties of hemoglobin and its dependence on oxygen saturation. Spectral images at the selected wavelengths of the present invention measure changes in the oxyhemoglobin saturation for any retina by measuring the percent differences of oxyhemoglobin based on reflectance changes at various wavelengths. Thus, functional areas of the retina are determined.

Equation (1) presents the analytical form of the radiation transfer for energy that is reflected from hemoglobin imaged in the retina. With this equation, and using absorption coefficients and typical optical densities, the contributions of the oxyhemoglobin signal as measured by an OID-RF can be estimated. The expected signal from a retinal arteriovenous difference for oxy-hemoglobin yield a measurable change in the reflectance spectra at the interrogation waveband, such as 700 nm±5 nm.

$$(1) \quad I_R = I_I 10^{-2\{\alpha_S D_S^R \mu^R + \alpha_u D_u^R (1-\mu^R) + \alpha_{RPE} D_{RPE} + \alpha_S D_S^C \mu^C + \alpha_u D_u^C (1-\mu^C)\}}$$

where $I_R$ is the measured reflected light, $I_I$ is the incident light at the retina, $\alpha_i$ are the absorption coefficients, $D_j$ are the optical densities, and $\mu_k$ are the saturations. The S subscripts relate to the values at saturation and the U subscripts relate to the values for unsaturated hemoglobin. The R superscripts relate to the retinal layer and C to the choroidal layer.

Because local changes in the reflectance of light in the spectral region indicative of the ratio of oxyhemoglobin to deoxyhemoglobin and/or total blood volume have been found to mirror local changes in neuronal function in brain preparations, a similar approach can be applied to the human retina. The time constant of these small changes in reflected light is relatively long (on the order of 2-5 seconds following a visible light stimulus), which provides sufficient time to collect stimulus-evoked spectral intensity changes.

Results

An OID-RF meeting the requirements of the present invention was reduced to practice by taking an existing fundus camera and modifying the optical path by selectively filtering the continuous light source in the fundus camera to achieve an interrogation wave band. A stimulus pattern was presented at one wavelength (530 nm), while interrogating the oxy-hemoglobin change at a different wavelength (700 nm), using the same optical path. The OID-RF device was built by modifying a Canon Fundus Photo Perimeter CPP-1.

Figure 3:
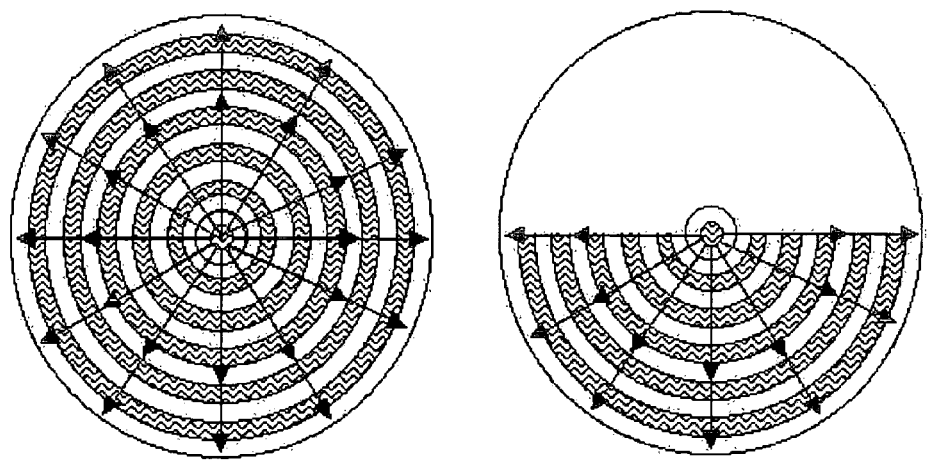
FIG. 3 illustrates two stimulus patterns according to an embodiment of the present invention.

FIG. 3 illustrates two stimulus patterns used in the working example. These patterns are, while used to generate exemplary results that follow are not meant as limitation. Other patterns may be used by those skilled in the art to elicit the retinal response illustrated and anticipate by the method disclosed herein. Patterns radiate from the center at 2 cycles per second. The spatial frequency varies from 10 cycles per degree (cpd) in the parafovea to 0.2 cpd in the periphery. The polarity of the hemifield pattern could be adjusted to present a pattern in the superior half. A high luminance LCD projector coupled to a computer was used to produce the visual stimulus pattern to the retina at a spectral band centered on 530 nm. The stimulus used was based on a moving concentric circular grating pattern, with a fixation point in the center. The grating was rectangular in profile with a fundamental spatial frequency scaled with eccentricity, from 10 cycles per degree in the parafovea to 0.2 cycles per degree in the periphery (15-20 degrees radius). The grating moved with an average temporal frequency of 2 Hz and was near 100% in contrast. The intensity of the stimulus was 100 cd/m2. A fixation target (small "+") was placed in the field-of-view of the eye being examined. The fixation target served to keep the subject's eye in a nearly constant position with respect to the stimulus pattern. The imaging cycle was triggered from an external computer, which interfaces with the LCD stimulus presentation and the CCD camera image collection. The spatial frequency, temporal frequency and intensity of the stimulus used, along with the stimulus wavelength, were chosen to provide maximum stimulation of retinal ganglion cells while being completely within the safety limits of light exposure to the eye. The retinal illumination used for both the stimulation and the interrogation was well below that employed during standard fundus examination and photography.

Figure 4:
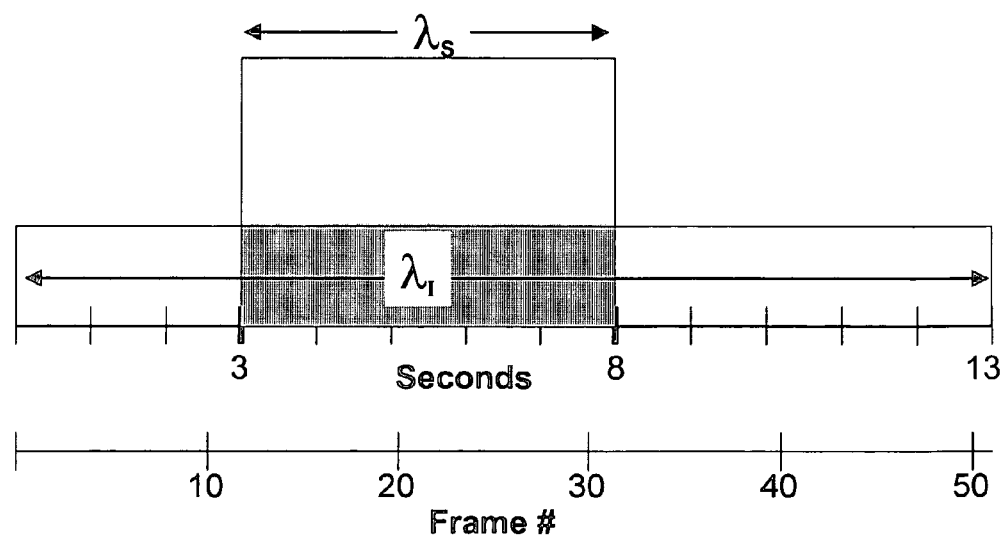
FIG. 4 illustrates a typical interrogation epoch according to an embodiment of the present invention.

This basic concentric grating stimulus was programmed to move in a radial direction and stimulates the entire retina or a given sector of it. For example, in one preferred embodiment one of the two hemifields (e.g. superior and inferior hemiretina) in a given stimulus session can be selected for illumination FIG. 4 illustrates a typical interrogation epoch according to an embodiment of the present invention. The retina was stimulated and simultaneously measured during a 5 second interval after a pre-stimulus baseline of 3 seconds was recorded. The stimulus period was followed by an additional 5 second recovery period of recording. This data collection epoch was repeated an average of 10 times for each eye with rest periods between epochs. Involuntary eye blinks were not included in the averaging of frames following each stimulus. There was no direct interference from the stimulation source (530 nm) or the interrogation (700 nm) wavelength since the two bands were separated using internal filters. (See, FIG. 1).

Figure 5:
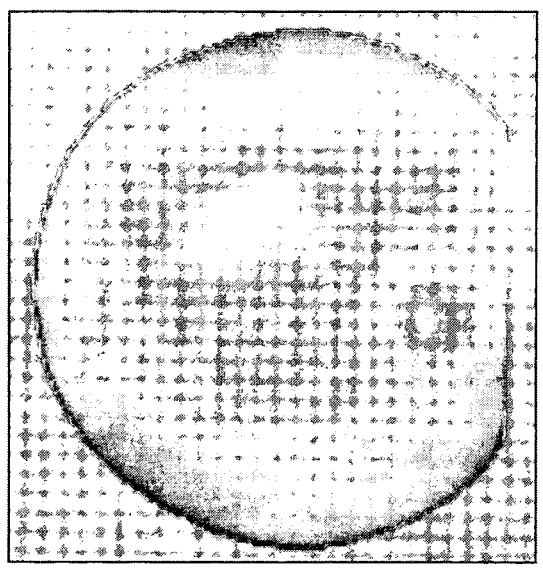
FIG. 5 illustrates a typical image frame according to an embodiment of the present invention.

An OID-RF was used to apply a stimulus pattern (FIG. 3) to the human subject's retina. One of these patterns are applied during a 13s epoch (FIG. 4). The epoch starts with 3s of baseline data, followed by 5s of stimulus, and 5s of recovery time when, as with the baseline measurements, no stimulus is applied. A digital video camera operating at about 3 Hz collects 162×167 pixel frames of a 40° field of view centered on the fovea. FIG. 5 illustrates a typical image frame according to an embodiment of the present invention. The image shown is from the right retina and the optic disc is to the right side of the image.

Two normal subjects, M6 and M8, were subjected to testing. The data set for M8 comprises 30 epochs, with both superior and inferior retinal stimulus. The data set for M6 comprises 60 epochs, with full field, superior and inferior retinal stimulus. Each epoch comprises 53 image frames of data.

The data results were evaluated to determine which epochs presented unwanted artifacts. For this the standard deviation of the pixels intensity over reach epoch was calculated. Epochs with high standard deviation were determined to have artifacts and were removed from the analysis. The epochs with the same stimulus condition were averaged to reduce random noise. The result was an average epoch also comprising 53 frames, where each of the 53 averaged frames came from the same frame in the sequence for each epoch. Each stimulus condition resulted in an average epoch.

The number of frames was further reduced by calculating average frames that represented blocks of time in the epoch. For example, two blocks of five frames each represent the base period, three blocks for the stimulus period and three blocks for the recover period. Finally, to perform a First Frame Analysis, the first block was subtracted from the rest of the block. First Frame Analysis permits measurement of only the changes produced during the stimulation, eliminating the background level.

In an embodiment of the present invention, the functional response of the retina due to the stimulation was isolated using principal component analysis (PCA). PCA determines an appropriate subspace of dimensionality smaller than the dimensionality of the original feature space of the images. Using PCA the functional signal can be reconstructed using a subset of the principal components. The data set has the time series of each pixel in the image, and the principal components can be found as the solution of $$SV = \Lambda V' \quad (1)$$

where S is the sample covariance matrix of the data set and its elements are given by $$S_i = \frac{1}{N_i - 1} \sum (x_{ij} - \bar{x}_i)(x_{ij} - \bar{x}_i)^T \quad (2)$$

where the $x_{ij}$ are the pixel values of the observed sources.

The matrix V contains the eigenvectors $v_n$ and $\Lambda$ is the diagonal matrix of the eigenvalues $\lambda_n$, which represents the variance of the data along the principal axes. The matrix V is orthogonal and the eigenvectors are normalized and orthogonal to each other, that is $$v_i^T v_i = 1 \quad (3)$$

$$v_i^T v_j = 0 \, \forall i \neq j \quad (4)$$

The n-th principal component is given by $$y_n = \lambda_n^{-1/2} v_n^T X \quad (5)$$

The functional signal $\hat{X}$ can be reconstructed using a combination of the principal components, and can be calculated by $$\hat{X} = \sum_n v_n (v_n^T X) = \sum_n v_n \lambda_n^{1/2} y_n$$

Figure 6:
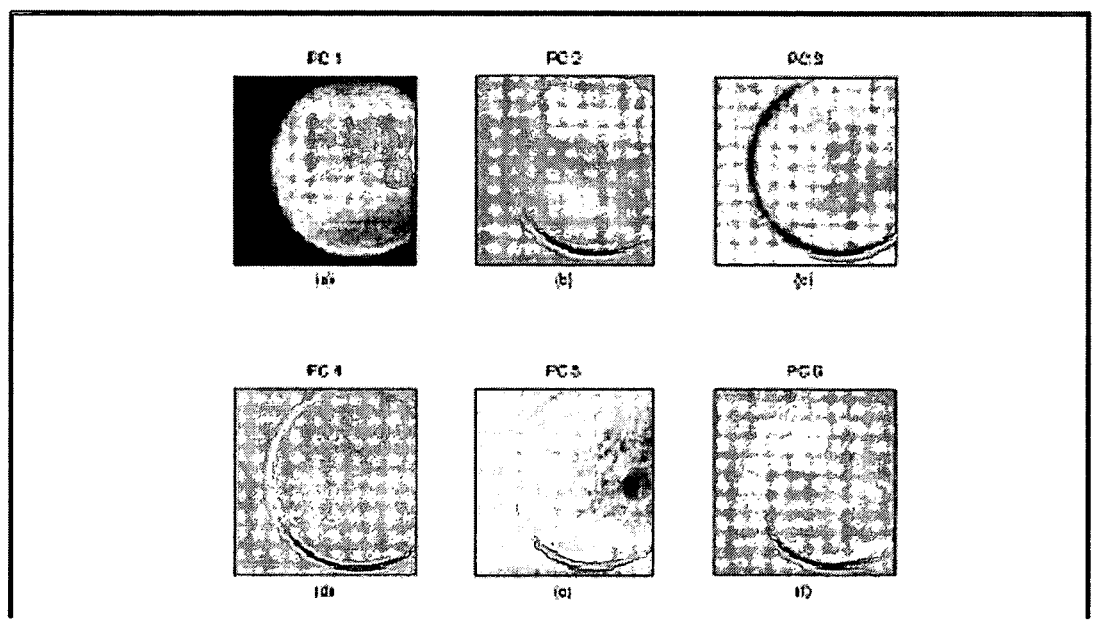
FIG. 6 illustrates a set of six principal components for a specific frame for subject M6, where the intensity of the principal components 2 through 6 have been resealed to make them visible.

Exemplary embodiments of the present invention focus upon two regions of the retina, a superior and an inferior Region of Interest (ROI), both of 30×40 pixels size. FIG. 6 illustrates a set of six principal components for a specific frame for subject M6, where the intensity of the principal components 2 through 6 have been resealed to make them visible. Calculations showed that the first principal component accounts for 95 to 98% of the information, and reproduces the general reflectance level depicted in FIG. 6 (PCI). In general it was found that the principal components 2 through 5 potentially contain the information on the functional signal, while the remaining principal components do not appear to have any useful information. The reconstructed image using the first principal component appears as a blurred version of the original video while the remaining the components present the detail.

Figure 7:
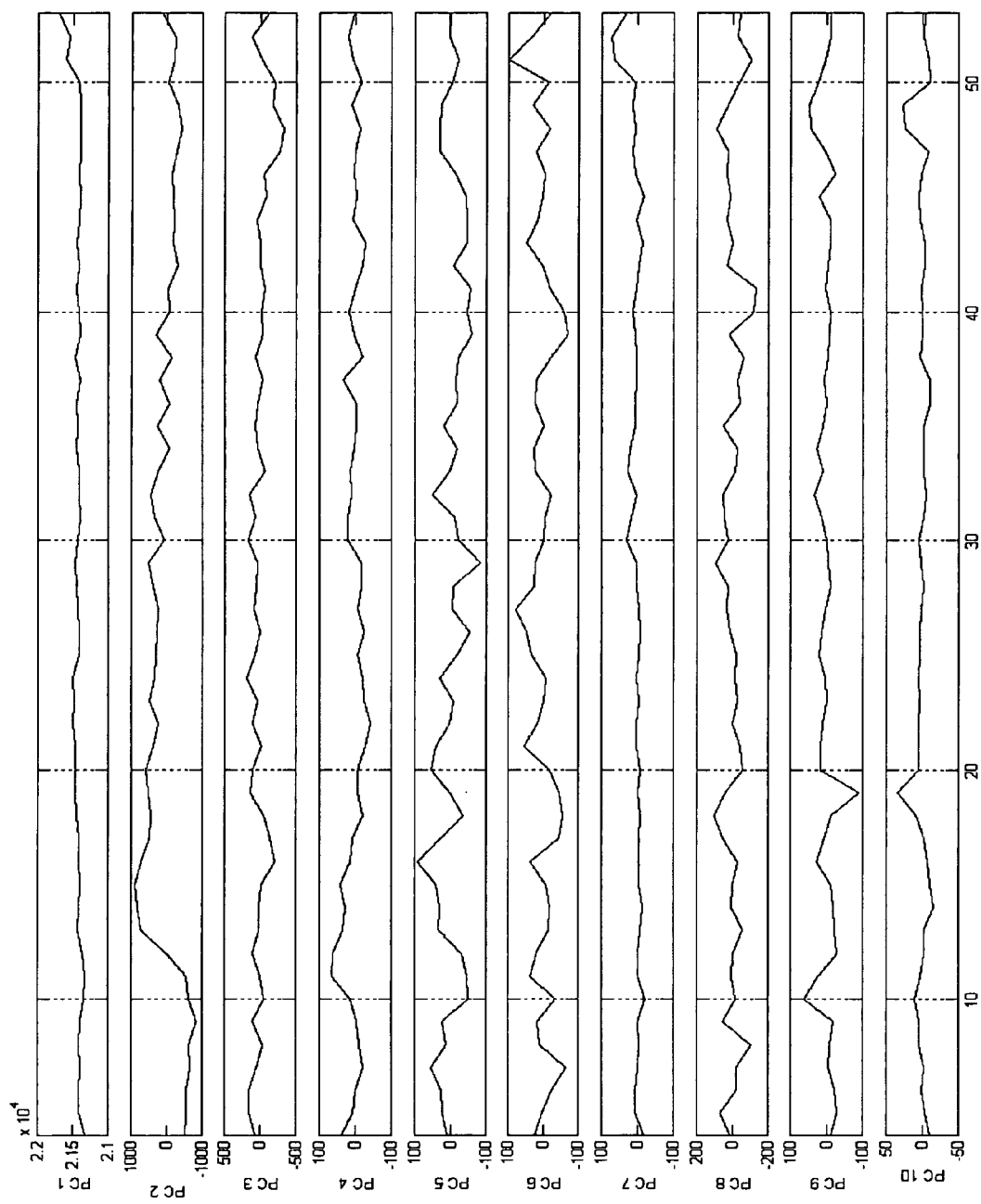
FIG. 7 illustrates the time series of the first 10 principal components (applied to the images without binning) of subject M6.

FIG. 7 illustrates the time series of the first 10 principal components (applied to the images without binning) of subject M6. Since the stimulus experiment consisted of 12 frames of baseline where no stimulus applied, followed by 20 frames of stimulus, the waveform that was expected was a more or less flat signal during the base and a rise in the reflectance about the 12th frame. For M6, the second principal component shows the rise in the reflectance, at about the 12th frame, which is consistent with the onset time of the stimulus. This rise in the reflectance is highly suggestive to be directly related to the functional signal.

Figure 8:
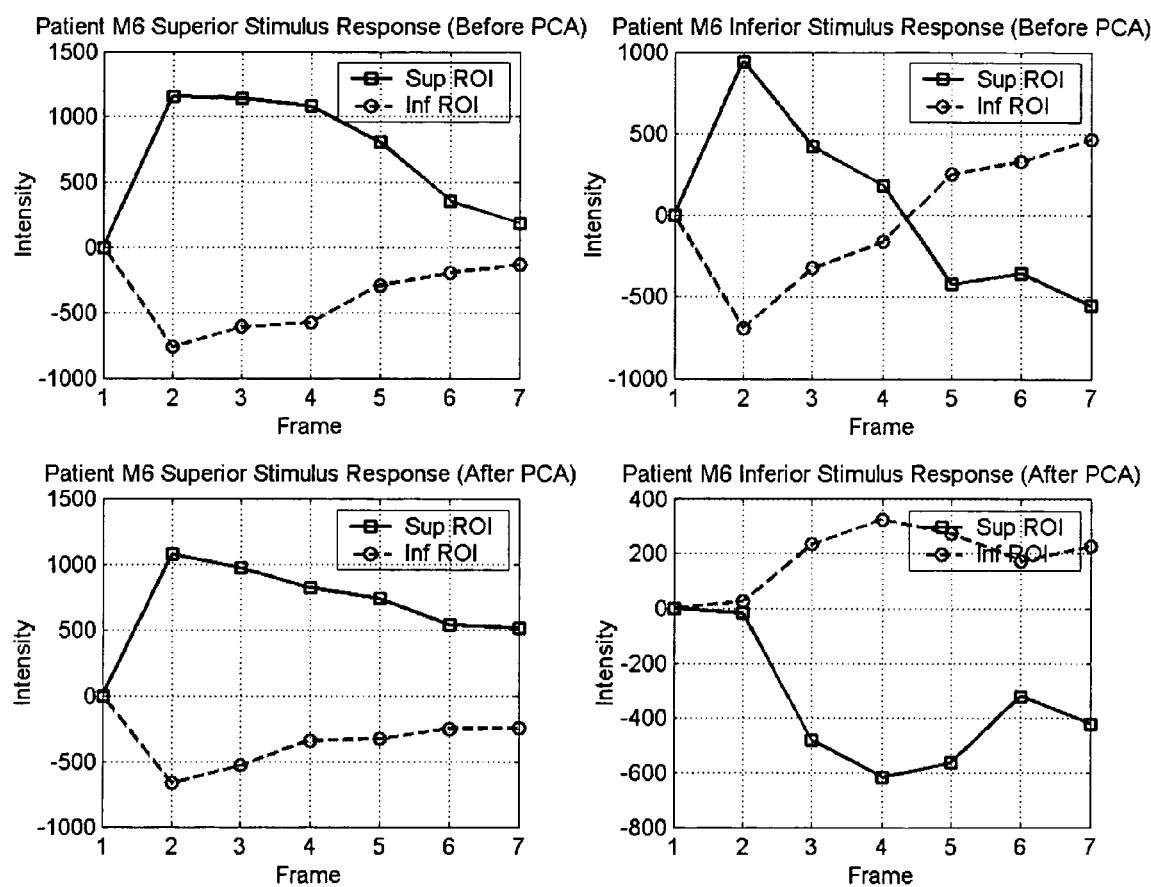
FIG. 8 illustrates the ROI's intensity before and after applying PCA for the subject M6.

Further analysis concentrated on the detection of a functional signal for a region of interest (ROI). The ROI's were focused on two regions of the retina, a superior and an inferior ROI, each 30×40 pixels in size. After applying first frame analysis to the images, the mean intensity value over the ROI was obtained and plotted the values through time. FIG. 8 illustrates the ROI's intensity before and after applying PCA for the subject M6. The two top plots (FIGS. 8A and 8B) are the normalized signals before PCA was applied while the lower two plots (FIGS. 8C and 8D) are after PCA. The two left plots (FIGS. 8A and 8C) illustrate stimulation of the superior half of the retina while the two right plots (FIGS. 8B and 8D) illustrated stimulation of the inferior half of the retina. The two left plots (8A and 8C) (where the superior half of the retina was stimulated) indicate a rise after frame #1.

The benefit of PCA is demonstrated in the analysis of the right two plots (8B and 8D) where an inferior stimulus was applied. In this case the dashed line with circular symbols should show a rise at frame #2. Before the PCA was applied, the converse was observed. That is, the reflectance in the stimulated region (dashed line) decreased at frame #2 (upper right), while an increase in reflectance was observed in the non-stimulated region (solid line). After PCA, the expected pattern in the reflectance signal was observed (lower right). The PCA processed signal shows a slight increase in frame #2 and continuing increase through frame #4 for the inferior region (dashed line, lower right plot). This pattern in the waveform is what is expected for an inferior stimulus.

Figure 9:
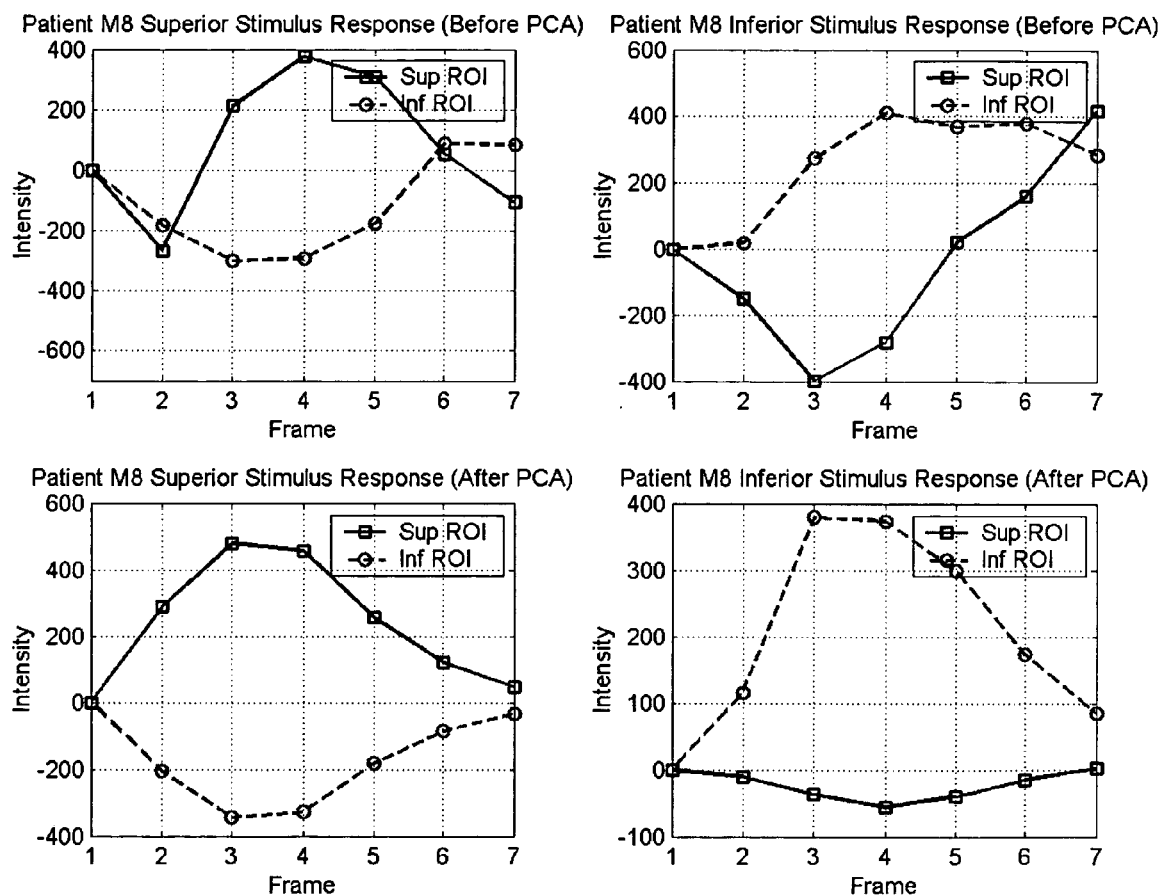
FIG. 9 illustrates the ROI's intensity before and after applying PCA for the subject M8.

FIG. 9 illustrates the ROI's intensity before and after applying PCA for the subject M8. In this case the response plots for the superior stimulus (solid line) showed a decrease in reflectance at the time of the stimulus before processing with the PCA (upper left). The PCA processed signals for the superior stimulus (lower left) behaved in a manner consistent with the stimulus pattern. For the inferior stimulus, both the non-PCA and the PCA processed signals showed a pattern consistent with a inferior stimulus (dashed line). The PCA improved the saliency of the pattern (lower right, dashed line).

The present invention processes functional retinal images obtained from a subject through the application of principal components using changes in the reflection of near infrared light (700 nm) as a means of detecting a response to a visual stimulus (530 nm). The tigroid pattern that is observed in many of the high order principal components corresponds to the pattern of deeper lying choroidal vessels making it another component to focus upon as a fiduciary for a functional signal. The signal being isolated by the principal components result in changes in the oxyhemoglobin concentration in the deep choroidal vessels.

Other principal components that define the functional signal in the ROI being stimulated can also isolate different physiological processes in the non-stimulated ROI. The reflectance signal being recorded can be viewed as a combination of all processes going on in the retinal layers, as well as other global changes in the hemodynamics. Local increases in oxyhemoglobin in response to a visual stimulus is explained by either a reactive increase in regional blood flow in the stimulated area or a decrease in tissue oxygen consumption. Reflectance changes in the non-stimulated regions also result from "sympathetic" changes due to increased demands in stimulated regions of the retina.

While the focus was on the identification of those principal components that defined the functional signal, more data on a greater number of subjects, will likely isolate other signals. For example, the same principal components that define the functional signal in the ROI being stimulated may also isolate different physiological processes in the non-stimulated ROI. The problem that PCA presents is that to obtain the functional signal a linear combination on the components must be performed, which is both tedious procedure and susceptible to errors.

In another embodiment of the present invention, blind source separation algorithms (Fast-ICA and ESD algorithms) were applied to the data.

Figure 10A:
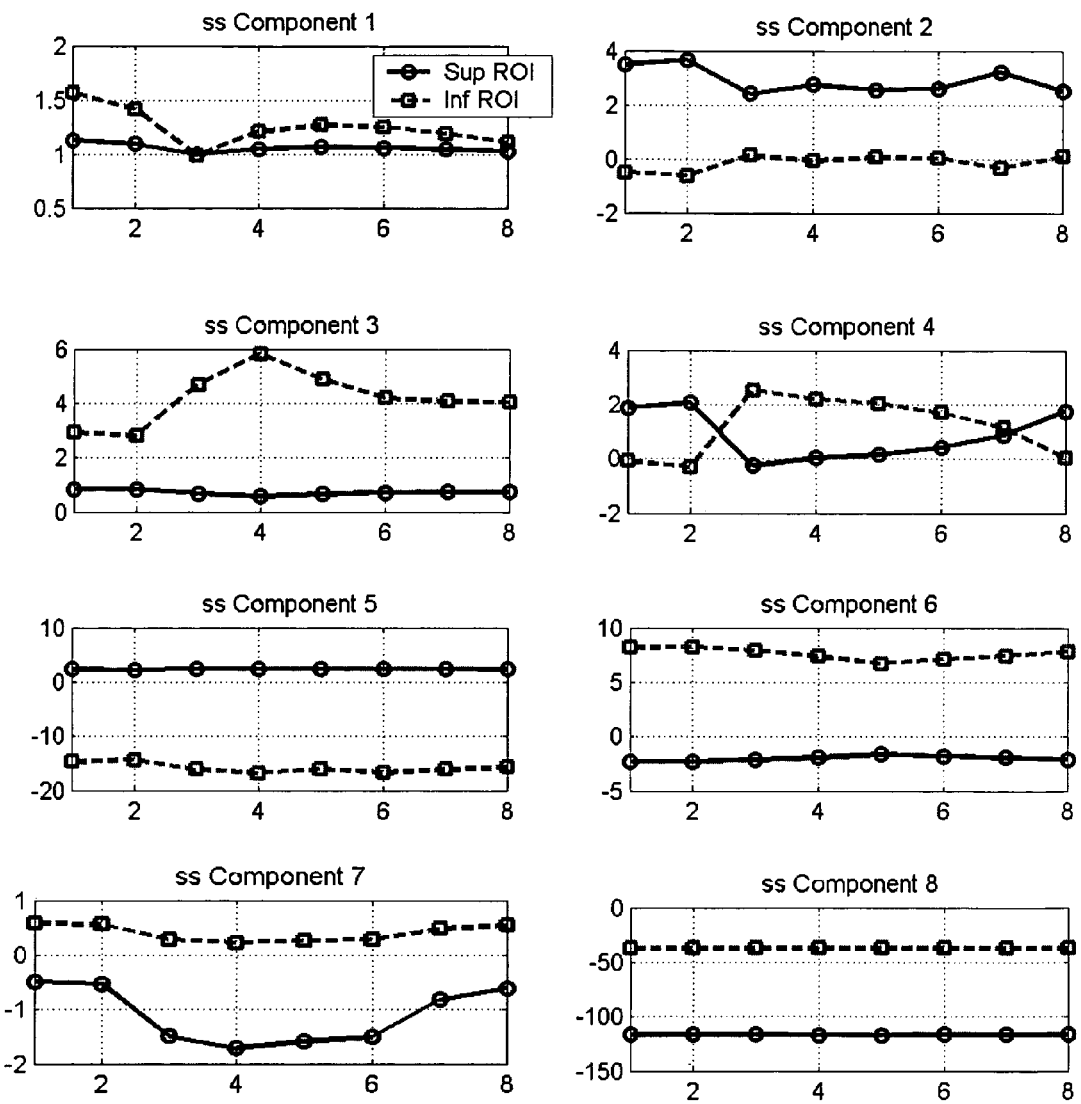
FIGS. 10A and 10B illustrate the results of applying Fast-ICA to the data for subject M6.
Figure 10B:
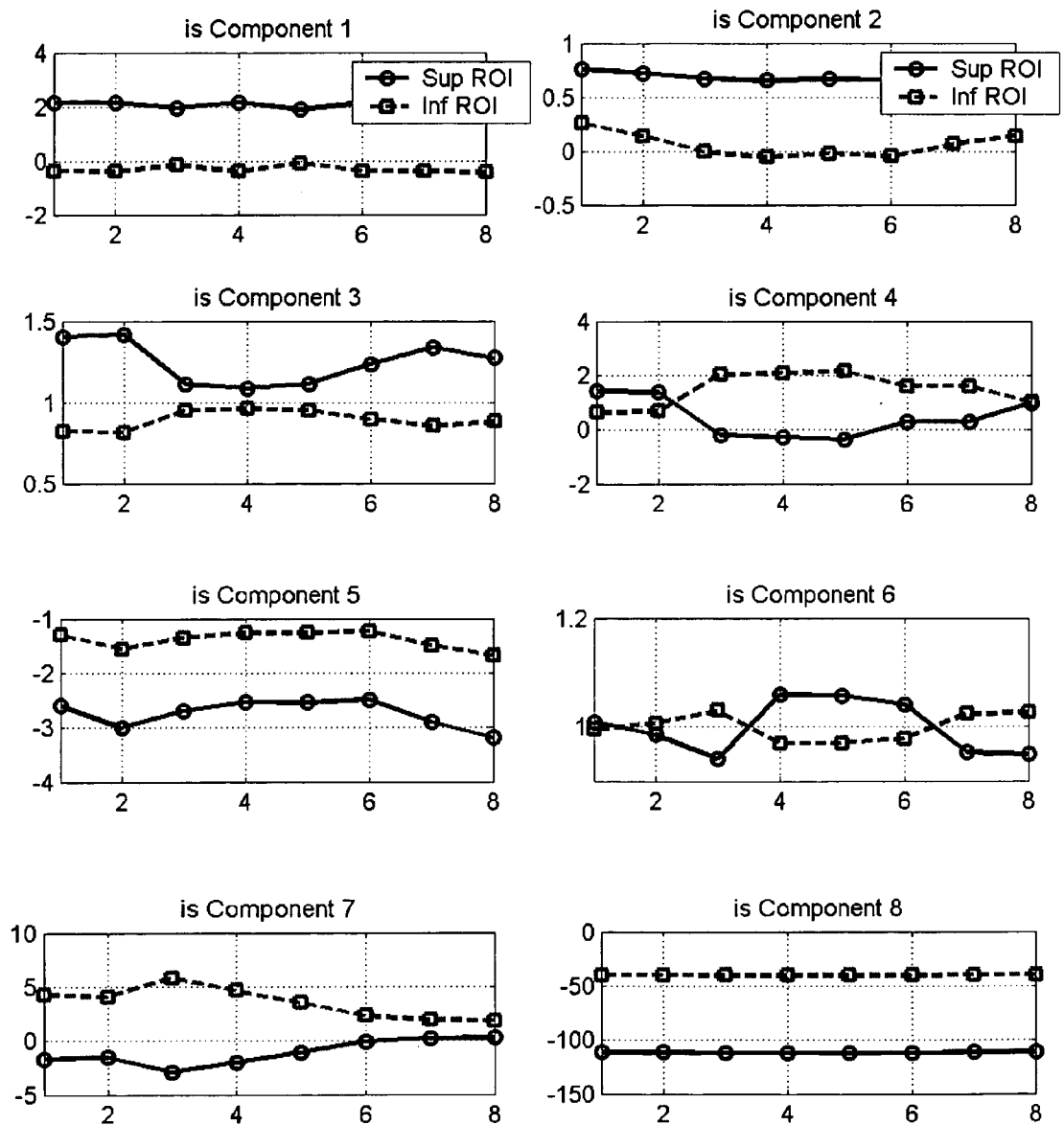

FIGS. 10A and 10B illustrate the results of applying Fast-ICA to the data for subject M6. Due to the nature of the ICA and BSS algorithms there is an ambiguity on the sign of the estimated sources, therefore in the next set of results the important information is the changes due to the stimulation, without taking into account the direction of those changes. Referring to FIG. 10A, the components 3 and 4 present a rise in the intensity of the inferior ROI after the stimulus is applied. Referring to FIG. 10B, a rise can also be detected in components 3 and 4 after frame #2. As we can see in both cases, changes in the retina are detected immediately after the retinal stimulation is applied.

Figure 11A:
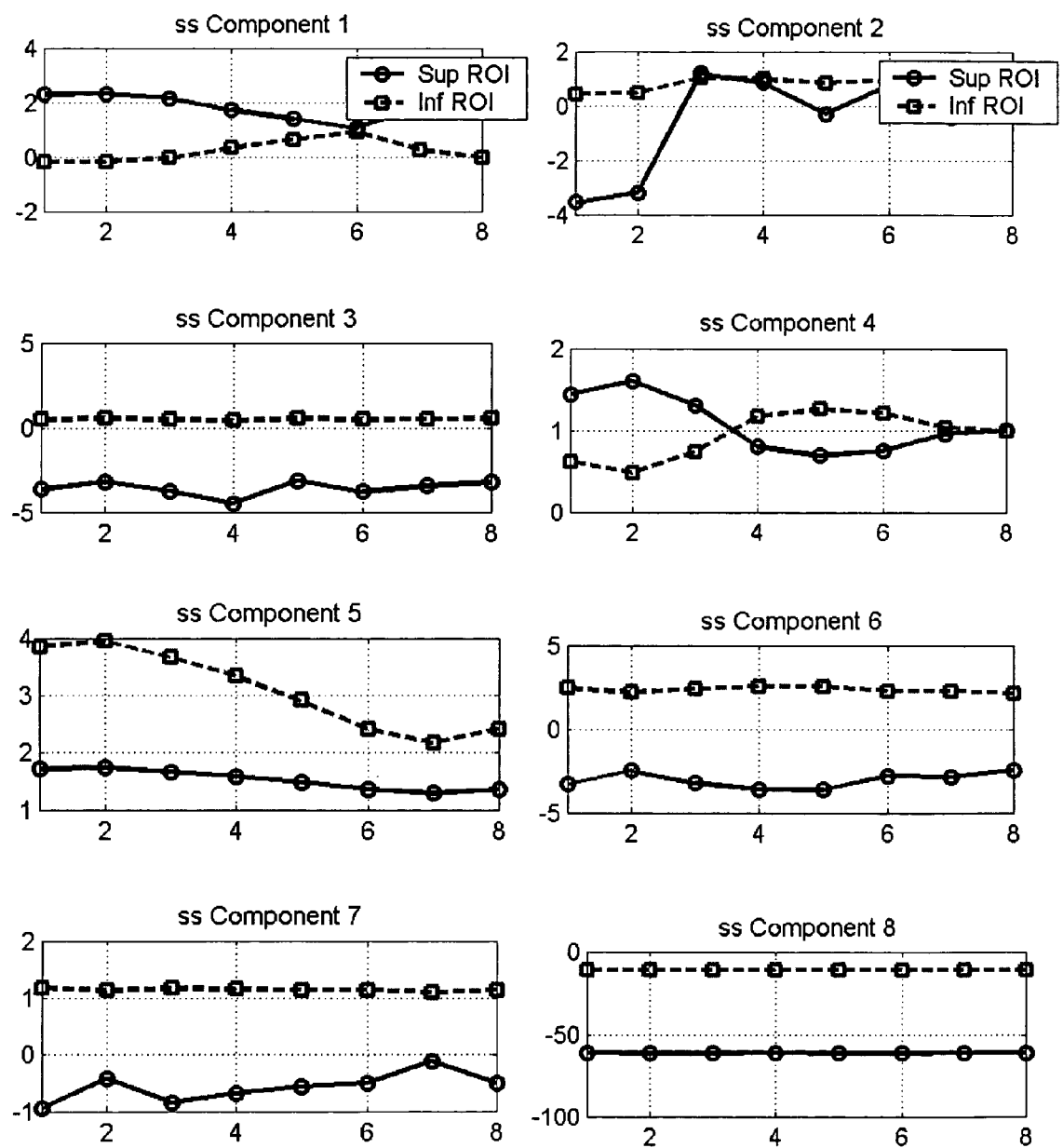
FIGS. 11A and 11B illustrate the results of applying Fast-ICA to the data for subject M8.
Figure 11B:
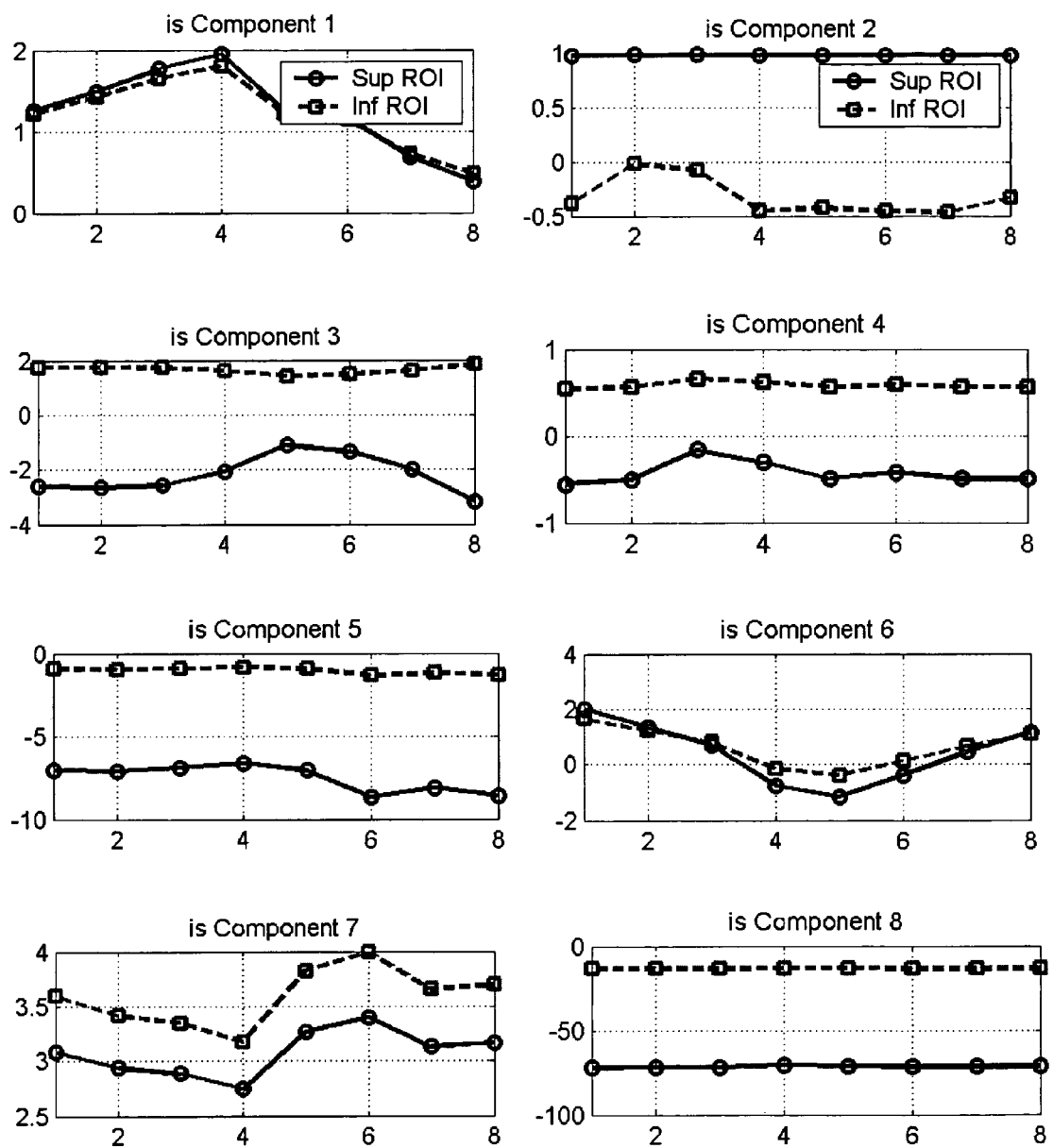

FIGS. 11A and 11B illustrate the results of applying Fast-ICA to the data for subject M8. Referring to FIG. 11A, the superior stimulus, component 2 appears to correspond to a stimulus applied at frame 3. For the inferior stimulus (FIG. 11B), there are no patterns in the inferior ROI components that are consistent with the stimulus cycle.

Figure 12A:
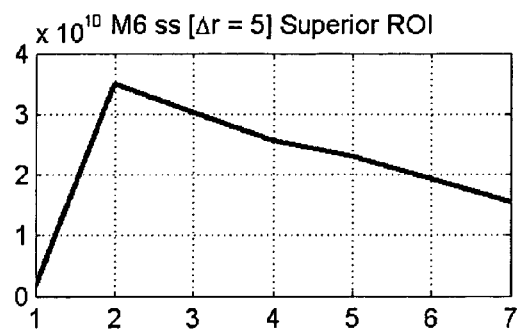
FIGS. 12A and 12B illustrate the results of applying the ESD algorithm to the data for subject M6 using a lag ($\Delta r$) of 5.
Figure 12A:
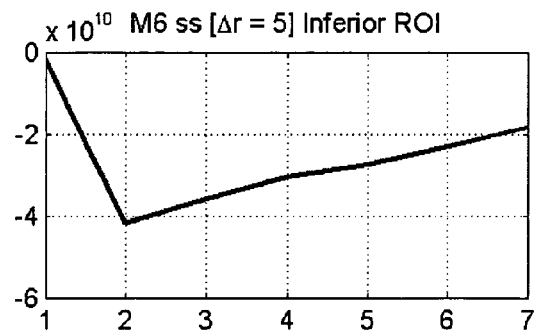
Figure 12A:
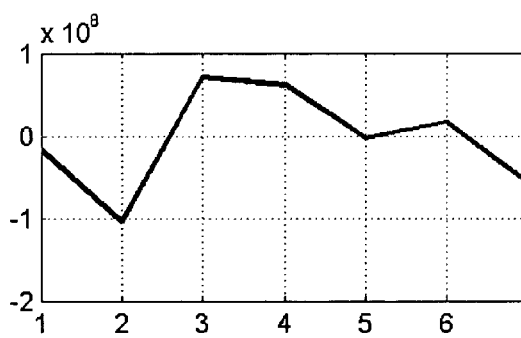
Figure 12A:
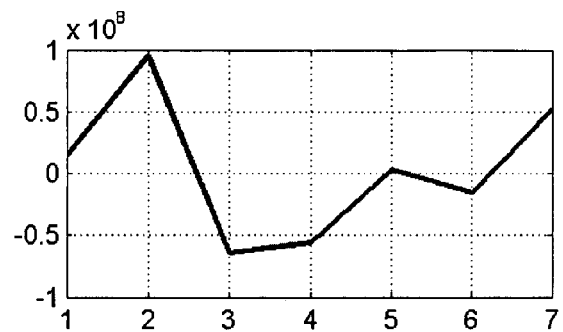
Figure 12A:
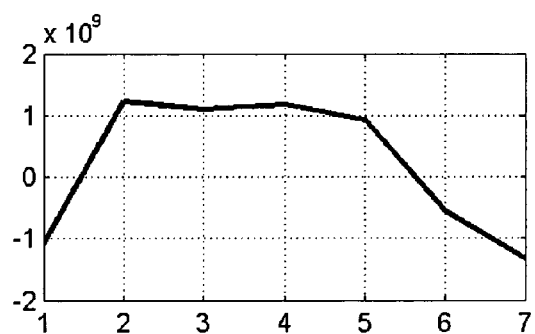
Figure 12A:
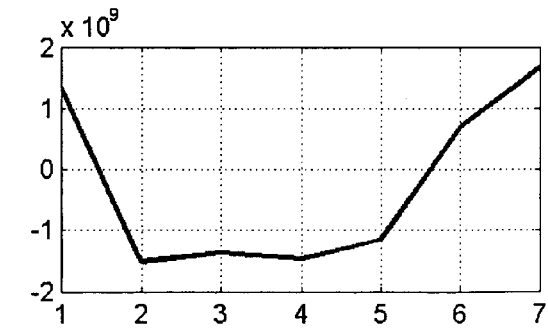
Figure 12B:
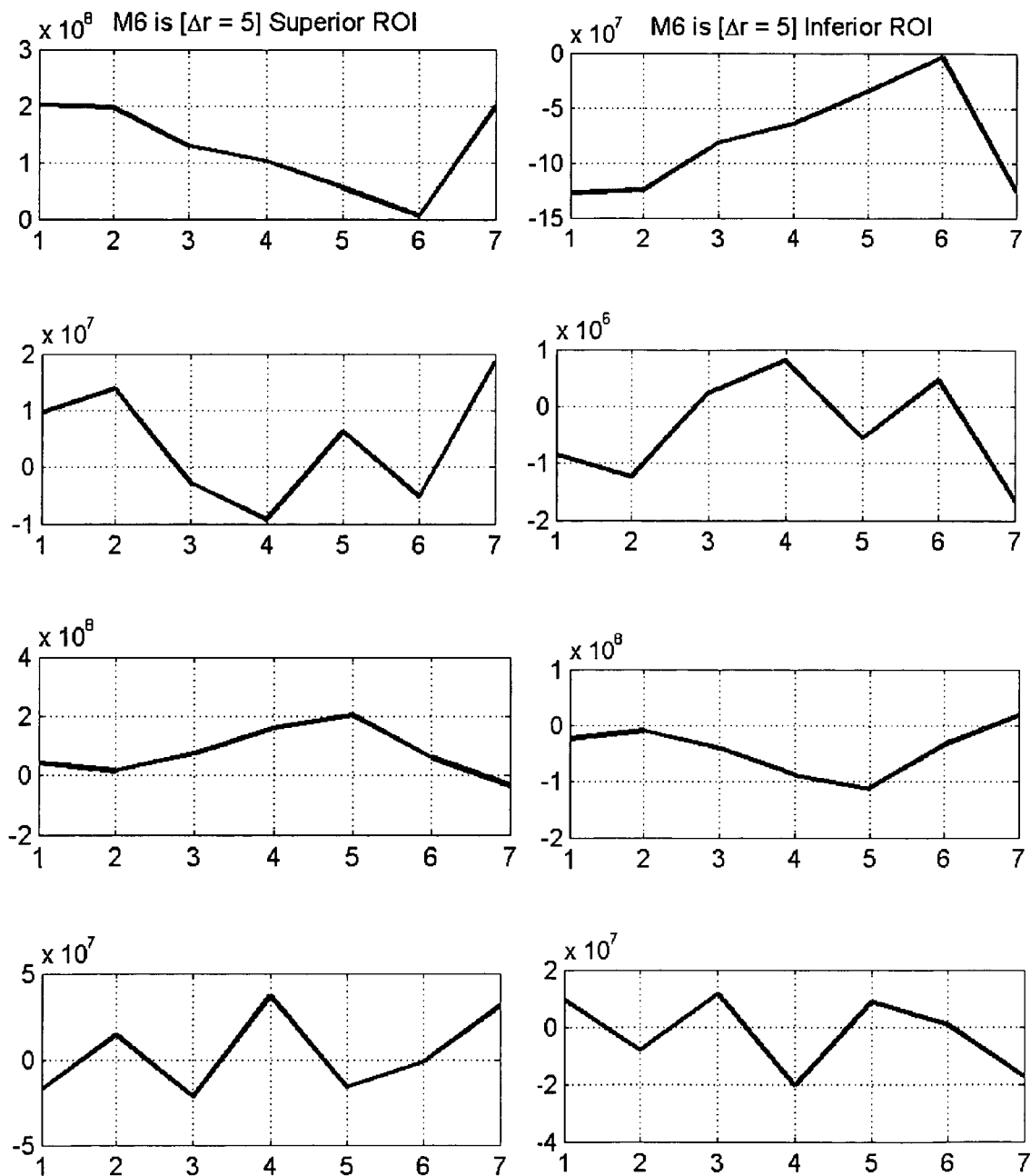

FIGS. 12A and 12B illustrate the results of applying the ESD algorithm to the data for subject M6 using a lag ($\Delta r$) of 5. Referring to FIG. 12A, the response for a superior stimulus is illustrated while FIG. 12B illustrates the response for an inferior stimulus. On the left are the responses for the superior stimulus and on the right are responses of the inferior stimulus. In FIG. 12A, the first and third components (top and bottom left) for the superior ROI and superior stimulus presents a functional response that is consistent with the stimulus cycle. In other, words, the response increases for frame 3.

Referring to FIG. 12B, the same pattern is reflected. When the stimulus is applied to the inferior ROI, the inferior ROI responds as expected, as can be seen in the first and second components (top two left side). There is no response in the non-stimulated superior ROI (right) that correlates to the stimulus cycle.

Figure 13A:
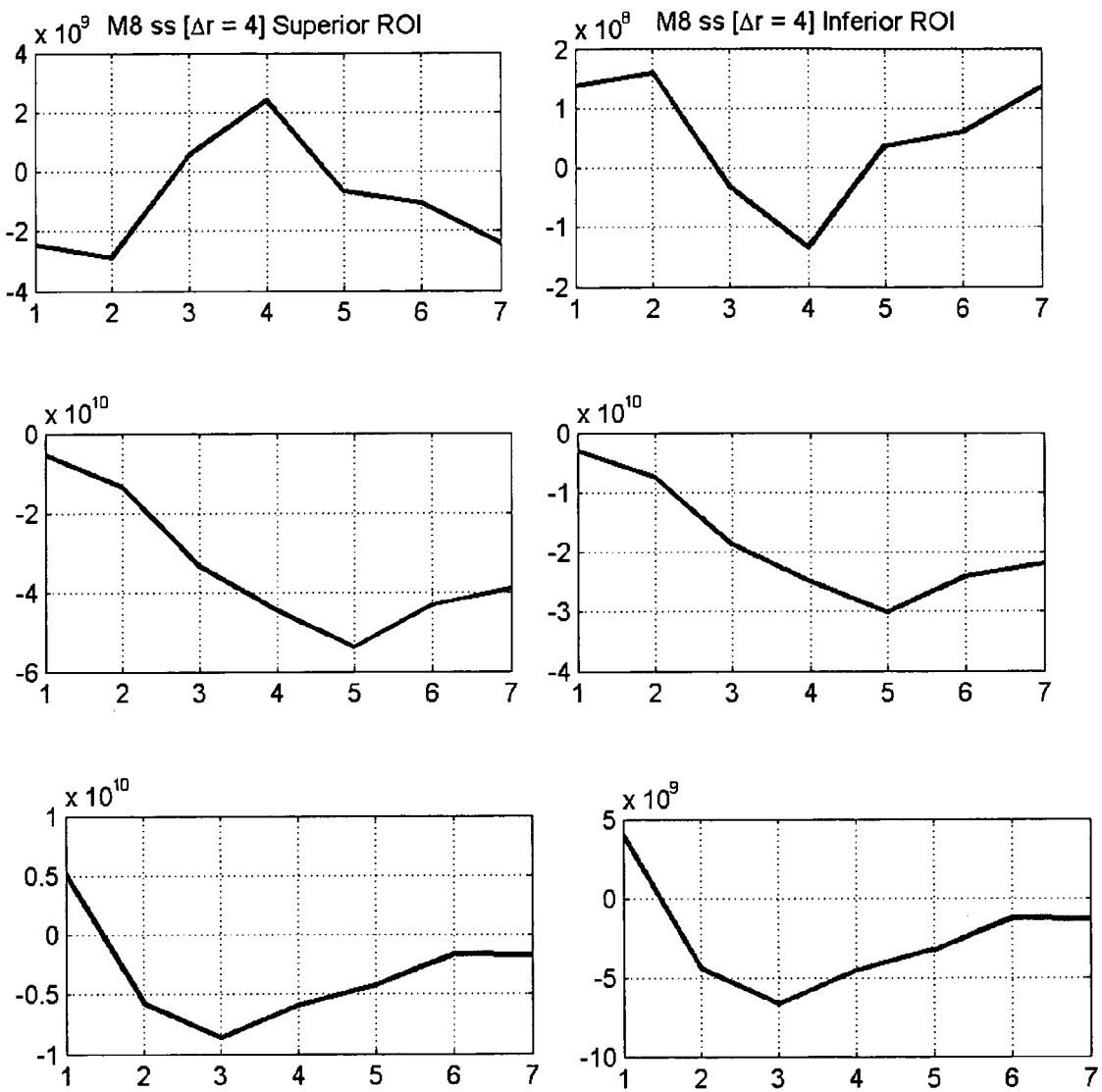
FIGS. 13A and 13B illustrate the results of applying the ESD algorithm to the data for subject M8 using a lag ($\Delta r$) of 5.
Figure 13B:
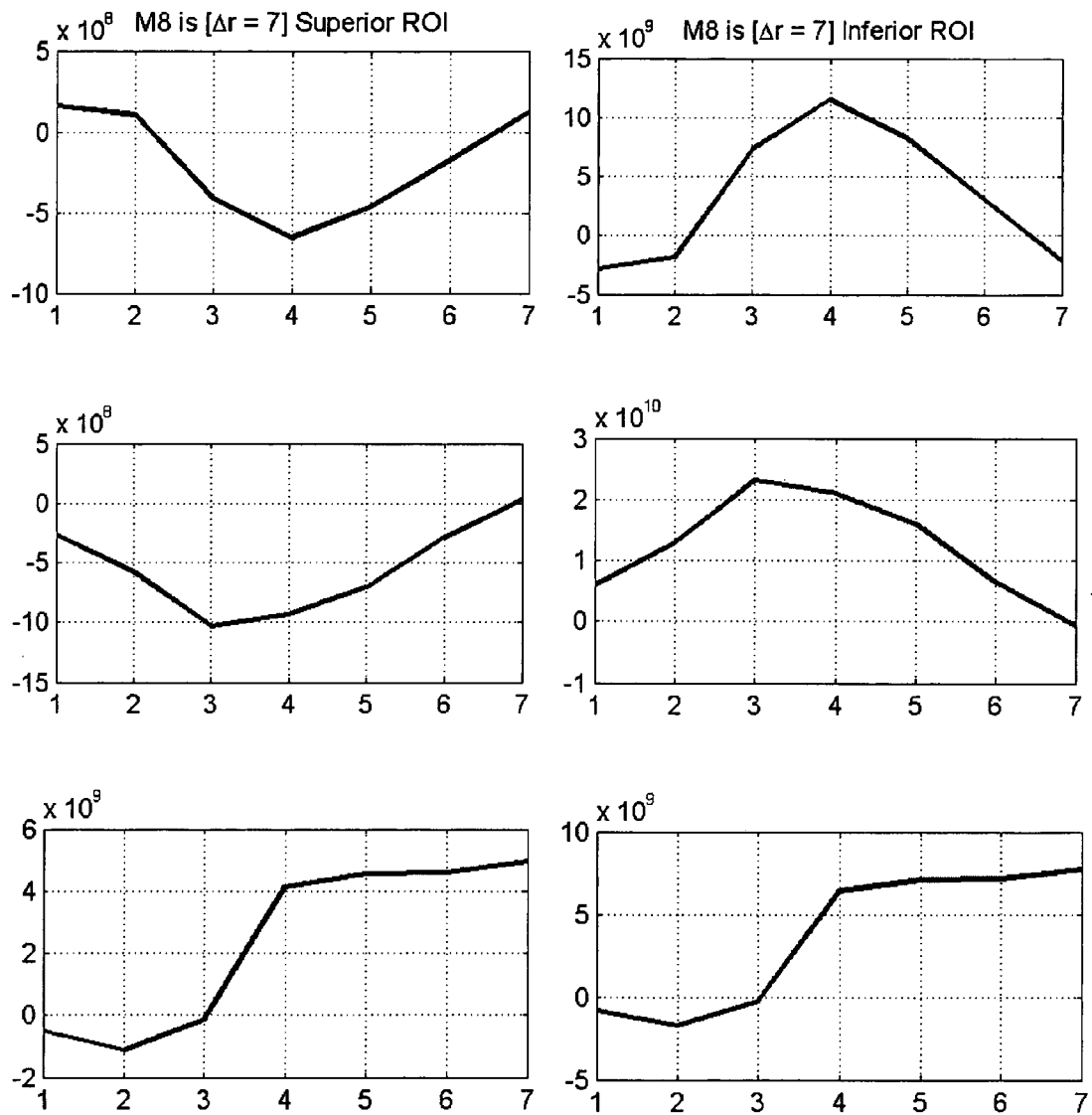

FIGS. 13A and 13B illustrate the results of applying the ESD algorithm to the data for subject M8 using a lag ($\Delta r$) of 5. On the left of FIG. 13A, the first component does indeed show a response for the superior ROI (left) that reflects the stimulus cycle, while the inferior ROI (right) does not. FIG. 13B gives the responses for an inferior stimulus. On the right of FIG. 13B, the first and second components of the BSS indicates a response that is consistent with the stimulus cycle. Thus through the application of ICA algorithms and blind source separation techniques linear and non-linear physiological responses of the retina to a visual stimulus can be accounted for. By adjusting the individual pixel values via the analysis described herein, the response in a given area of the retina, as depicted in the recorded images from the detector can be adjusted. In so doing, source of variability that are not due to the change in oxyhemoglobin saturation can be largely eliminated. What remains is a visual record of the change in oxyhemoglobin saturation pre- and post-stimulation. These images can be more properly correlated to show areas of the retina that did NOT respond to the stimulation wavelength and hence are areas of reduced retinal functionality. Thus the method of the present invention more accurately maps functional areas of the retina.

A system and method for detecting a functional signal and hence functional areas of a retina as depicted in retinal images has been disclosed. The application of Principle Components Analysis (PCA), Independent Components Analysis (ICA), and Blind Source Separation (BSS) have been disclosed in a particular form. This is not meant as a limitation as those skilled in the art will appreciate that other aspects of these statistical techniques may be employed without departing from the scope of the invention as described. Further, although an underlying premise of linearity in variables is made with the application of these techniques, it is also deemed with the scope of the present invention to apply non-linear ICA to the separation of sources present in the stimulation of the retina as well. It will be understood by those skilled in the art of the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible.

We claim:

1. A method for detecting functional areas in retinal images comprising:
    illuminating a hemifield of the retina using a stimulating wavelength;
    illuminating the entire retina at a non-stimulating wavelength;
    simultaneously recording the resultant reflectance of the stimulated hemifield of the retina and the non stimulated hemifield of the retina in the non-stimulating wavelength region; and
    determining functional areas of the retina based upon reflectance differences in the stimulated and non-stimulated hemifields in the non-stimulating wavelength.

2. The method for detecting functional areas in retinal images of claim 1 wherein
    illuminating the hemifield of the retina using a stimulating wavelength comprises illuminating the hemifield of the retina at about 530 nm.

3. The method for detecting functional areas in retinal images of claim 1 wherein illuminating the entire retina at a non-stimulating wavelength comprises illuminating the entire retina in the near infrared region of the spectrum.

4. The method for detecting functional areas in retinal images of claim 1 wherein illuminating the entire retina at a non-stimulating wavelength comprises illuminating the entire retina at about 700 nm.

5. The method for detecting functional areas in retinal images of claim 1 wherein
determining functional areas of the retina based upon reflectance differences in the stimulated and non-stimulated hemifields in the non-stimulating wavelength comprises repeating the method to obtain multiple images of the same eye and applying principal components analysis to the resulting reflectance differences to determine functional areas of the retina.

6. The method for detecting functional areas of retinal images of claim 1 wherein determining functional areas of the retina based upon reflectance differences in the stimulated and non-stimulated hemifields in the non-stimulating wavelength comprises repeating the method to obtain multiple images of the same eye and applying a fast-ICA algorithm to the resulting images to determine functional areas of the retina.

7. The method for detecting functional areas of retinal images of claim 1 wherein determining functional areas of the retina based upon reflectance differences in the stimulated and non-stimulated hemifields in the non-stimulating wavelength comprises repeating the method to obtain multiple images of the same eye and applying an extended spatial decorrelation algorithm to the resulting images to determine functional areas of the retina.

8. The method for detecting functional areas of retinal images of claim 1 wherein illuminating a hemifield of the retina using a stimulating wavelength comprises illuminating the hemifield with a variable pattern in the stimulating wavelength.

9. The method for detecting functional areas of retinal images of claim 1 wherein illuminating a hemifield of the retina using a stimulating wavelength comprises illuminating the hemifield for variable lengths of time in the stimulating wavelength.

10. The method for detecting functional areas of retinal images of claim 1 wherein illuminating a hemifield of the retina using a stimulating wavelength comprises illuminating a superior hemifield of a retina.

11. The method for detecting functional areas of retinal images of claim 1 wherein illuminating a hemifield of the retina using a stimulating wavelength comprises illuminating an inferior hemifield of a retina.

12. A method for determining retinal hemoglobin saturation before and after stimulation comprising:
illuminating a hemifield of the retina using a stimulating wavelength;
illuminating the entire retina at a non-stimulating wavelength;
simultaneously recording the resultant reflectance of the stimulated hemifield of the retina and the non stimulated hemifield of the retina in the non-stimulating wavelength region; and
determining retinal hemoglobin saturation based upon reflectance differences in the stimulated and non-stimulated hemifields in the non-stimulating wavelength.

13. The method for determining retinal hemoglobin saturation before and after stimulation according to claim 12 wherein:
illuminating the hemifield of the retina using a stimulating wavelength comprises illuminating the hemifield of the retina at about 530 nm.

14. The method for determining retinal hemoglobin saturation before and after stimulation of claim 12 wherein illuminating the entire retina at a non-stimulating wavelength comprises illuminating the entire retina in the near infrared region of the spectrum.

15. The method for determining retinal hemoglobin saturation before and after stimulation of claim 12 wherein illuminating the entire retina at a non-stimulating wavelength comprises illuminating the entire retina at about 700 nm.

16. The method for determining retinal hemoglobin saturation before and after stimulation of claim 12 wherein:
determining functional areas of the retina based upon reflectance differences in the stimulated and non-stimulated hemifields in the non-stimulating wavelength comprises repeating the method to obtain multiple images of the same eye; and applying principal components analysis to the resulting reflectance differences to determine functional areas of the retina.

17. The method for determining retinal hemoglobin saturation before and after stimulation of claim 12 wherein determining functional areas of the retina based upon reflectance differences in the stimulated and non-stimulated hemifields in the non-stimulating wavelength comprises repeating the method to obtain multiple images of the same eye and applying a fast-ICA algorithm to the resulting images to determine functional areas of the retina.

18. The method for determining retinal hemoglobin saturation before and after stimulation of claim 12 wherein determining retinal hemoglobin saturation based upon reflectance differences in the stimulated and non-stimulated hemifields in the non-stimulating wavelength comprises repeating the method to obtain multiple images of the same eye and applying an extended spatial decorrelation algorithm to the resulting images to determine hemoglobin saturation.

19. The method for determining retinal hemoglobin saturation before and after stimulation of claim 12 wherein illuminating a hemifield of the retina using a stimulating wavelength comprises illuminating the hemifield with a variable pattern in the stimulating wavelength.

20. The method for determining retinal hemoglobin saturation before and after stimulation of claim 12 wherein illuminating a hemifield of the retina using a stimulating wavelength comprises illuminating the hemifield for variable lengths of time in the stimulating wavelength.

* * * * *